United States Patent [19]

Hilti et al.

[11] 3,984,593

[45] Oct. 5, 1976

[54] 5,6,11,12-TETRASELENOTETRACENE-O-CHLOROANIL COMPLEXES

[75] Inventors: Bruno Hilti, Basel; Carl W. Mayer, Riehen, both of Switzerland

[73] Assignee: Ciba-Geigy Corporation, Ardsley, N.Y.

[22] Filed: July 31, 1975

[21] Appl. No.: 600,761

[30] Foreign Application Priority Data

Aug. 9, 1974 Switzerland.................. 10958/74

[52] U.S. Cl................. 427/248; 260/239 R; 427/126
[51] Int. Cl.²............ C07D 517/06; C07D 517/04; H01B 1/06
[58] Field of Search............ 427/248 B, 126; 260/239 R

[56] References Cited
UNITED STATES PATENTS

| | | | |
|---|---|---|---|
| 3,162,641 | 12/1964 | Acker et al. | 260/286 |
| 3,226,389 | 12/1965 | Hertler | 260/283 |
| 3,403,165 | 9/1968 | Matsunaga | 260/327 |
| 3,634,336 | 1/1972 | Perez-Albuerne | 260/519 |
| 3,723,417 | 3/1973 | Perez-Albuerne | 260/239 |
| 3,754,986 | 8/1973 | Perez-Albuerne | 427/74 |

FOREIGN PATENTS OR APPLICATIONS 2,364,445  6/1974  Germany

OTHER PUBLICATIONS

Chaudhari et al., Applied Physics Letters, 24, 439–441 (1974).

*Primary Examiner*—James R. Hoffman
*Attorney, Agent, or Firm*—Luther A. R. Hall

[57] ABSTRACT

Novel 5,6,11,12-tetraselenotetracene-o-chloroanil complexes are disclosed which exhibit improved electrical conductivity, and low resistivity at room temperature. Said complexes are useful, e.g., as organic electrical conductors, solid state devices, and for providing antistatic coatings.

6 Claims, No Drawings

5,6,11,12-TETRASELENOTETRACENE-O-CHLOROANIL COMPLEXES

The present invention provides new 5,6,11,12-tetraselenotetracene-o-chloroanil complexes of the formula

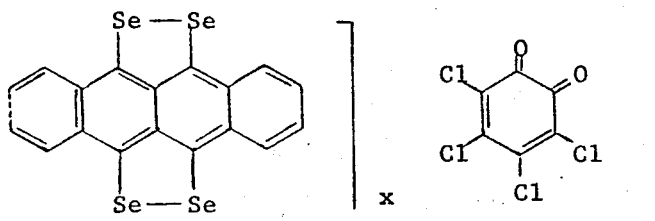

wherein $x$ is 2.5 to 3.5 and is preferably 3.0, and a process for the manufacture thereof. The invention also has for its object the use of the novel complexes as organic conductor element with metallic-electrical and metallic-optical properties.

The compounds according to the invention are cation radical-anion radical charge transfer complex salts in which the 5,6,11,12-tetraselenotetracene forms the electron donor and the o-chloroanil forms the electron acceptor. The complex salts according to the invention have a particularly good electrical conductivity. Their temperature dependence has metallic character, i.e. the electrical conductivity increases from room temperature (20°–25°C) to approximately 140°K (−133.15°C). This is surprising, since none of the hitherto known organic compounds with metallic properties contain any quinones as acceptors.

The complexes according to the invention are characterised by a very low specific resistance [$\rho \leq 1.5 \times 10^{-4}$ ohm cm at room temperature, measured along the needle axis of monocrystals], a good heat stability, a low specific weight in comparison to metals (1.8 g/cm$^3$), easy accessibility and negligible solubility in conventional organic solvents, e.g. acetonitrile, acetone, methanol, dimethyl sulphoxide, N,N-dimethyl formamide and 1,2,4-trichlorobenzene.

The 5,6,11,12-tetraselenotetracene-o-chloroanil complexes can be in the form of coatings or, preferably, as a substance, i.e. in the form of microcrystalline powders and especially of monocrystals.

The complexes according to the invention as a substance or in the form of coatings, i.e. by direct coating of inorganic or organic substrates, can be manufactured in a manner which is known per se by reacting 5,6,11,12-tetraselenotetracene and o-chloroanil. Chemically speaking, this reaction is a partial oxidation of the 5,6,11,12-tetraselenotetracene by the o-chloroanil. The 5,6,11,12-tetraselenotetracene and the o-chloroanil are used normally in stoichiometric ratios, i.e. in a molar ratio of 2.5 to 3.5 to 1. If appropriate, a surplus of o-chloroanil can also be used, e.g. in a surplus of up to 3 times the stoichiometric amount.

The complexes according to the invention are manufactured as a substance by reacting the 5,6,11,12-tetraselenotetracene and the o-chloroanil in the presence of a suitable organic solvent.

Suitable organic solvents are principally high boiling halogenated, especially chlorinated, aromatic hydrocarbons, e.g. 1,2,3-trichlorobenzene, 1,2,4-trichlorobenzene and o-dichlorobenzene, and also polar solvents, such as N,N-dialkyl amides of monocarboxylic acid with 1 to 4 carbon atoms, e.g. N,N-dimethyl formamide and N,N-dimethyl acetamide, or dialkyl sulphoxides, e.g. dimethyl sulphoxide. It is preferred to carry out the reaction in 1,2,4-trichlorobenzene. The complex salt formation takes place usually at a temperature of about 20°C.

The formation of the complexes according to the invention in crystalline form can vary within wide limits depending on the nature of the solvent used and of the other reaction conditions (concentration, temperature). When using a halogenated aromatic hydrocarbon, especially 1,2,4-trichlorobenzene, as solvent, the complex salt formation is usually terminated within a few minutes.

The precipitated complex salt can be isolated and purified in the customary manner, for example by filtering it off and washing it repeatedly with an appropriate organic solvent, e.g. benzene. Depending on the choice of reaction conditions, the 5,6,11,12-tetraselenotetracene-o-chloroanil complex salts according to the invention are obtained as a microcrystalline black powder or in the form of monocrystals as thin, greyish black, glistening needles. Monocrystals can be obtained for example by delaying the crystal formation by slowly cooling the reaction mixture in dimethyl sulphoxide. However, it is also possible to obtain them by recrystallising the complex in microcrystalline form from a suitable organic solvent, e.g. dimethyl sulphoxide.

The best monocrystals, both as regards their appearance and their electrical conductivity, are obtained by diffusion of o-chloroanil from the gas phase, or from a suitable carrier solution, through a solution of 5,6,11,12-tetraselenotetracene, e.g. in N,N-dimethyl acetamide.

Coatings of complexes according to the invention are produced direct on inorganic or organic substrates, e.g. quartz, mica or plastic sheets, by the vapour deposition of 5,6,11,12-tetraselenotetracene and o-chloroanil onto the substrate, preferably in vacuo.

On account of their very high electrical conductivity with metallic temperature behaviour, the 5,6,11,12-tetraselenotetracene-o-chloroanil complexes have a particularly suitable utility as electrical conductors with low specific weight (1.8 g/cm$^3$), for which purpose they are preferably used in the form of monocrystals, and also for the manufacture of organic solid state devices, such as Peltier elements, thermoresistances and organic metallic electrodes, or else for the manufacture of antistatic coatings, e.g. for photographic or electrophotographic information carriers.

Complexes according to the invention which are in the form of (micro)crystal needles have a pronounced optical anisotropy and can therefore also be used for example for the manufacture of infrared polariser sheets.

Because the charge transfer reaction of the complex components to give the complexes according to the invention takes place at room temperature (20°–25°C) during the manufacture as a substance, and a drastic change in the electrical conductivity and a change in colour occur at this temperature, these occurrences can be used for fixing information, e.g. in soft-ground etching or for producing electric writing.

Further fields of application of the complexes according to the invention — preferably in the form of microcrystalline powder — are: as additivs for obtaining defined electrical properties and increased heat conductivity in plastics; as greyish greenish blue electrically conductive pigment which is insoluble in conventional organic solvents; as catalyst for radical polymerisations, e.g. those of styrene.

EXAMPLE 1

110 mg (0.205 mmols) of 5,6,11,12-tetraselenotetracene are dissolved in 70 ml of boiling 1,2,4-trichlorobenzene and this solution is treated at once with a solution of 55 mg (0.225 mmols) of o-chloroanil in 5 ml of 1,2,4-trichlorobenzene. The 5,6,11,12-tetraselenotetracene-o-chloroanil complex ($x = app.$ 3.0) precipitates immediately in the form of a deep black microcrystalline powder. After the reaction solution has been cooled to 50°C, this powder is collected by suction filtration, washed repeatedly with benzene and dried for 24 hours at 40°C/0.01 Torr. Yield: 116 mg of the above complex salt (=94% of theory). Analysis of $C_{60}H_{24}Se_{12}Cl_4O_2$ (molecular weight 1866.18): estimated: C, 38.61%; H, 1.30%; Se, 50.77%; Cl, 7.59%. found: C, 38.47%; H, 1.41%; Se, 51.00%; Cl, 6.43%. Specific resistance of the microcrystalline powder at room temperature (RT: 20°–25°C)$\rho_{RT} = 0.1$ ohm cm.

Specific weight: 1.8 g/cm$^3$.

Metallic-optical properties: In the wave length range of 0.6–1.2$\mu$ the reflection is 6% and at 2.6$\mu$ it is 28%.

EXAMPLE 2

The microcrystalline powder obtained in Example 1 is recrystallised from 150°C hot dimethyl sulphoxide. The 5,6,11,12-tetraselenotetracene-o-chloroanil complex is obtained in monocrystal form as very thin black needles. Specific resistance of the monocrystals at room temperature (RT): $\rho_{RT} \leq 1.5 \times 10^{-3}$ ohm cm.

EXAMPLE 3

11.0 mg (0.0205 mmols) of 5,6,11,12-tetraselenotrance are dissolved in 60 ml of dimethyl sulphoxide at 150°C and this solution is treated with a solution of 1.62 mg (0.0066 mmols) of o-chloroanil in 2 ml of 1,2,4-trichlorobenzene. The reaction solution is cooled slowly to room temperature over the course of 12 hours, whereupon the complex salt ($x = app.$ 3.0) is obtained in the form of fine, black crystal needles.

Yield: 5 mg (= app. 50% of theory). Specific resistance of the crystals at room temperature $\rho \leq 1.5 \times 10^{-3}$ ohm cm.

EXAMPLE 4

From a storage flask which has been warmed to 60°C, o-chloroanil is sublimed at 150 Torr under N$_2$ into a solution of 5,6,11,12-tetraselenotetracene in N,N-dimethyl acetamide which is saturated at 20°C. The complex according to the invention forms as long, thin, black needles having an almost ideal appearance.

Specific resistance at room temperature: $\rho_{RT} \leq 1.5 \times 10^{-4}$ ohm cm.

EXAMPLE 5

The monocrystals of the complex according to the invention manufactured in Examples 2 to 4 are provided with 2 or 4 electrical contacts and the specific resistance is measured in the 2 or 4 electrode arrangement.

Specific resistance of the best crystals at room temperature: $\rho \leq 1.5 \times 10^{-4}$ ohm cm. Ob cooling to 140°K (−133.15°C), the specific resistance falls to $\rho \leq 1.2 \times 10^{-4}$ ohm cm. At 77°K (−196.15°C), there is still a specific resistance of $\rho \leq 2 \times 10^{-4}$ ohm cm.

EXAMPLE 6

Vapour deposition of tetraselenotetracene and o-chloroanil in a ratio of 3:1 is effected simultaneously in a high vacuum onto quartz platelets. A layer of a complex according to the invention with a specific resistance of $p \leq 3 \times 10^{-1}$ ohm cm is obtained. On cooling, the layer exhibits only a very negligible increase in its specific electrical resistance:

$\rho_{77°K} \cong 1.2\rho_{RT}$.

Mica and plastic sheets can be coated in analogous manner.

We claim:

1. 5,6,11,12-tetraselenotetracene-o-chloroanil complexes of the formula

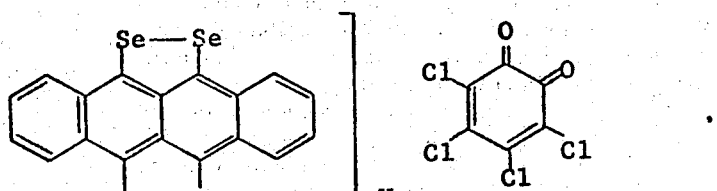

wherein $x = 2.5$ to 3.5.

2. 5,6,11,12-tetraselenotetracene-o-chloroanil complexes according to claim 1 in the form of microcrystalline powders or monocrystals.

3. 5,6,11,12-tetraselenotetracene-o-chloroanil complexes according to claim 1, wherein $x = 3.0$.

4. A process for the manufacture of 5,6,11,12-tetraselenotetracene-o-chloroanil complexes as claimed in claim 1, as a substance or in the form of coatings, characterized in that 5,6,11,12-tetraselenotetracene and o-chloroanil are reacted together.

5. A process as claimed in claim 4 for the manufacture of 5,6,11,12-tetraselenotetracene-o-chloroanil as a substance, characterized in that the 5,6,11,12-tetraselenotetracene and the o-chloroanil are reacted together in the presence of an organic solvent.

6. A process as claimed in claim 4 for the manufacture of 5,6,11,12-tetraselenotetracene-o-chloroanil complexes in the form of coatings, characterized in that the 5,6,11,12-tetraselenotetracene and o-chloroanil are vapourised onto an inorganic or organic substrate.

* * * * *